United States Patent [19]

Hunter et al.

[11] Patent Number: 5,250,294
[45] Date of Patent: Oct. 5, 1993

[54] IMPROVED PERFUSION MEDIUM FOR TRANSPLANTATION OF ORGANS

[75] Inventors: Robert L. Hunter, Tucker; Alexander Duncan, Dunwoody, both of Ga.

[73] Assignee: Emory University, Atlanta, Ga.

[21] Appl. No.: 977,530

[22] Filed: Nov. 17, 1992

Related U.S. Application Data

[60] Continuation of Ser. No. 802,331, Dec. 4, 1991, Pat. No. 5,198,211, which is a continuation of Ser. No. 522,206, May 11, 1990, Pat. No. 5,078,995, which is a continuation of Ser. No. 403,017, Sep. 5, 1989, abandoned, which is a continuation of Ser. No. 303,791, Jan. 30, 1989, abandoned, which is a division of Ser. No. 45,459, May 7, 1987, Pat. No. 4,801,452, which is a continuation-in-part of Ser. No. 43,888, Apr. 29, 1987, abandoned, which is a continuation of Ser. No. 863,582, May 15, 1986, abandoned.

[51] Int. Cl.⁵ .................................................. A61K 31/745
[52] U.S. Cl. .................................................. 424/78.31
[58] Field of Search .................................................. 424/78.31

[56] References Cited

U.S. PATENT DOCUMENTS

| Re. 29,909 | 2/1979 | Kurtz | 252/80 |
|---|---|---|---|
| 2,674,619 | 4/1954 | Lundsted | 560/158 |
| 2,854,378 | 9/1958 | Buckwalter et al. | 514/152 |
| 3,089,818 | 5/1963 | Stone | 424/78.38 |
| 3,140,232 | 7/1964 | Noseworthy | 424/78.38 |
| 3,450,502 | 6/1969 | Hymes | 422/35 |
| 3,577,522 | 5/1971 | Hymes | 424/78.31 |
| 3,590,125 | 6/1971 | Hymes | 424/78.38 |
| 3,740,421 | 6/1973 | Schmolka | 424/65 |
| 3,867,521 | 2/1975 | Miskel et al. | 424/78.38 |
| 3,956,259 | 5/1976 | Garcia et al. | 530/83.3 |
| 3,980,772 | 9/1976 | Ginger et al. | 424/94.64 |
| 4,073,886 | 2/1978 | Kehm | 530/83.3 |
| 4,100,271 | 7/1978 | Kreszanoski | 424/78.38 |
| 4,186,253 | 1/1980 | Yokoyama et al. | 435/240 |
| 4,395,393 | 7/1983 | Schmolka | 424/78.38 |
| 4,407,790 | 10/1983 | Oakes et al. | 424/78.38 |

OTHER PUBLICATIONS

Schmolka, I., "A Review Of Block Polymer Surfactants", *Journal of the American Oil Chemists Society*, 54, No. 3, pp. 110–116 (1977).

Block and Graft Copolymerization, vol. 2, (ed. by R. J. Ceresa, John Wiley & Sons, 1976), "The Applications of Block Copolymer Polyol Surfactants", L G. Lundsted and I. R. Schmolka; pp. 174–205 and pp. 255–272 (references).

Kanter, K. R., et al. "Superiority of perfluorocarbon cardioplegia over blood or crystalloid cardioplegia", *Circulation*, vol. 64, pp. II-75–II-80 (1981).

Harjula, A., et al., "Perfluorocarbon solution as a myocardial preservative", *J. Applied Cardiology*, vol. 2, pp. 121–136 (1987).

Hoie, J., et al., "Effects of Pluronic ® F68, Poloralkol, On Vascular Resistance In Vivo", *Journal of Surgical Research*, vol. 11, pp. 515–517 (1971).

Ketchum, L. D., et al., "Experimental Use Of Pluronic ® F-68 In Microvascular Surgery", *Plastic and Reconstructive Surgery*, vol. 53, pp. 288–292 (1974).

(List continued on next page.)

Primary Examiner—John W. Rollins
Attorney, Agent, or Firm—Jones & Askew

[57] ABSTRACT

In accordance with the present invention, a composition and method is provided for perfusion of organs. The present invention includes perfusion of organs in situ and before transplantation. The method comprises perfusing an organ with a perfusion medium containing an effective amount of a surface active copolymer. The surface active copolymer can be an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably approximately 1200 to 3500, and b is an integer such that the hydrophile portion represented by $(C_2H_4O)$ constitutes approximately 50% to 90% by weight of the compound.

12 Claims, 1 Drawing Sheet

OTHER PUBLICATIONS

Ketchum, L. D. "Experimental Use Of Pluronic F-68 In Microvascular Surgery", *Plastic and Reconstructive Surgery*, vol. 54, p. 478 (Oct. 1974).

Benner, K. U., et al., "Cold-Induced Platelet Aggregation In Vivo And Its Inhibition By A Nonionic Surface Active Substance", *Thrombosis Research*, vol. 2, pp. 331-332 (1973).

Benner, K. U., et al., "Uber die Wirkung von Pluronic ® F68, einem Poloxypropylen-Polyoxyyyathylen-Kondensat, auf die ADP-induzierte Thrombocytenaggregation in vitro", *Pfuger Arch.*, vol. 315, pp. 45-52 (1970).

Gaehtgens, P., et al., "Disaggregation of Human Red Blood Cells by Various Surface-Active Agents as Related to Changes of Cell Shape and Hemolysis", *Act Heamat.* vol. 33, pp. 82-89 (1975).

Grover, F. L., et al., "A Nonionic Surfactant And Blood Viscosity", *Arch. Surg.*, vol. 106, pp. 307-310 (1973).

Vasko, K. A., et al., "Poloxalkol ® (Pluronic F-68): A Priming Solution for Cardiopulmonary Bypass", *Trans. Am. Soc. Artif. Int. Organs*, 18, 526-531 (1972).

Organ Perfusion and Preservation, (ed. by Norman, J. C., Appleton-Century-Crofts, (1968)), Paton, B. C., et al. "The use of a nonionic detergent added to organ perfusates" pp. 105-120.

Grover, F. L. et al., "The Effect of Pluronic ® F-68 On Circulatory Dynamics And Renal And Carotid Artery Flow During Hemorrhagic Shock", *Journal of Surgical Research*, vol. 17, pp. 30-35 (1974).

Hymes, A. C., et al., "The Influence Of An Industrial Surfactant Pluronic ® F-68, In The Treatment of Hemorrhagic Shock", *Journal of Surgical Research*, vol. 11, pp. 191-197 (1971).

Advances in Blood Substitute Research (ed. by Bolin, et al., Alan R. Liss, Inc. New York, (1983)) Sugi, et al., The use of Fluosol-DA (FDA) in emergency situations: a report of 67 clinical cases, Abstract/451.

Vercellotti, G. M., et al., "Activation of Plasma Complement by Perfluorocarbon Artificial Blood: Probable Mechanism of Adverse Pulmonary Reactions in Treated Patients and Rationale for Corticosteroid Prophylaxis", *Blood*, vol. 59, pp. 1299-1304 (1982).

Forman, M. B., et al., "Reduction of infarct size with intracoronary perfluorochemical in a canine preparation of reperfusion", *Circulation*, vol. 71, 1060-1068 (1985).

Forman, M. B., et al., "Beneficial long-term effect of intracoronary perfluorochemical on infarct size and ventricular function in a canine reperfusion model", *J. Am. Co. of Cardiol.*, pp. 1082-1090 (May, 1987).

Tokioka, M. D., et al., "Effects of intracoronary infusion of arterial blood or Fluosol-DA 20% on regional myocardial metabolism and function during brief coronary artery occlusions", *Laboratory Investigation*, vol. 75, pp. 474-481 (1987).

Lane, T. A., et al., "Paralysis of phagocyte migration due to an artificial blood substitute", *Blood*, vol. 64, pp. 400-405 (1984).

Heron, M. W., et al., "A Method for Measuring a Nonionic Surface-Active Agent (Pluronic F-68) in Biological Fluids," *Analytical Biochemistry*, vol. 24, pp. 491-495 (1968).

Uno, T., et al, "Determination of Surface-Active Agents, VIII. Infrared Determination of the Proporation of Ethylene Oxide and Propylene Oxide in Pluronic," *Chem. Pharm. Bull.*, vol. 15(1), pp. 77-82 (1967).

Hymes, A. C., et al., "Influence of an industrial surfactant (Pluronic F-68) on human amniotic fluid embolism," *American Journal Obstetrics and Gynecology*, vol. 107(8), pp. 1217-1222 Aug. 15, 1970).

Grover, F. L., et al., "Beneficial Effect of Pluronic F-68 on the Microcirculation in Expiramental Hemorrhagic Shock," *Surgical Forum*, vol. 21, pp. 30-31 (1970).

Maugh, T. H., "Perfluorochemical Emulsions: Promising Blood Substitutes," *Science*, vol. 179, pp. 669-672 (Feb. 1973).

Justice, C., et al., "Prevention of Thrombosis with Agents which Reduce Platelets Adhesiveness," *The American Surgeon*, vol. 40, pp. 186-189 (Mar. 1974).

Danielson, G., et al, "Use of Pluronic F-68 to Dimish Fat Emboli and Hemolysis During Cardiopulmonary Bypass," *The Journal of Thoracic and Cardiovascular Surgery*, vol. 59(2), pp. 178-184 (Feb. 1970).

Reindorf, C. A., et al., "Perfluorocarbon Compounds: Effects on the Rheological Properties of Sickle Erythrocytes in vitro," *American Journal of Hematology*, vol. 19, pp. 229-236 (1985).

Padilla, F., et al., "Effect of Fluorocarbon emulsions on the mechanical fragility of normal and sickle cells: in vitro studies" *Federation Proceedings*, vol. 34, pp. 1510-1512 (1975).

OTHER PUBLICATIONS

Rodeheaver, G. T., "Pluronic ® F-68: a Promising New Skin Wound Cleanser", *Ann Emerg Med*, 9:11, pp. 572–576 (1980).

Janoff, A. S., et al., "The Modification of Human Erythrocyte Membrane Structure by Membrane Stabilizers: An Electron Spin Resonance Study", *American Journal of Hematology* vol. 10, pp. 171–179 (1981).

Moore, A. R. et al, "Reduction of Splenic Vascular Resistance During Profusion By Pluronic ® F-68", *Journal of Surgical Research*, vol. 8, pp. 563–566 (1968).

Ketchum, L. D., "Pharmacological alterations in the clotting mechanism: Use in microvascular surgery", *Journal of Hand Surgery*, vol. 3, pp. 407–415 (1978).

Block, N. L., et al., "Acutely Traumatized Canine Ureter: Effects of Low Molecular Weight Dextran and Surfactant Pluronic F-68", *Urology*, vol. III 190–194 (1974).

Knize, D. M., et al., "Use of Antisludging Agents in Experimental Cold Injuries," *Surgery, Gynecology & Obstetrics*, vol. 129, pp. 1019–1026 (1969).

Smillie, J. A., et al., "Cryopreservation of Human Platelets with Polyvinylpyrrolidone", *Transfusion*, vol. 21, pp. 552–556 (1981).

Lane, T. A., et al., "Reduction in the toxicity of a component of an artificial blood substitute by supercritical fluid fractionation", *Transfusion*, vol. 28, pp. 375–378 (1987).

Spiess, B. D., et al., "Protection from Cerebral Air Emboli with Perfluorocarbons in Rabbits", *Stroke*, vol. 17, pp. 1146–1149 (1986).

Goodman, R. L. et al., "Perfluorocarbon Emulsions in Cancer Therapy: Preliminary Observations on Presently Available Formulations", *Int. J. Radiation Oncology Biol. Phys.*, vol. 10, pp. 1421–1424 (1984).

Technical bulletin entitled "Performance Chemicals".

Technical bulletin entitled "Pluronic ® Block copolymer surfactants".

Perfluorochemical Blood Substitues, Technical Information Ser. No. 5, Jun. 30, 1978, Revised, Jul. 1, 1981. Manufacturer: The Green Cross Corporation.

Patent Cooperation Treaty International Search Report for PCT Patent Application No. PCT/US87/01747.

Patent Cooperation Treaty International Search Report for PCT Patent Application No. PCCT/US87/01067.

Fig_1

IMPROVED PERFUSION MEDIUM FOR TRANSPLANTATION OF ORGANS

This is a continuation of U.S. patent application Ser. No. 07/802,331 which was filed on Dec. 4, 1991, now U.S. Pat. No. 5,198,211, which is a continuation of U.S. patent application Ser. No. 07/522,206 which was filed on May 11, 1990, now U.S. Pat. No. 5,078,995, which is a continuation of Ser. No. 07/403,017 filed on Sep. 5, 1989, now abandoned, which is a continuation of U.S. patent application Ser. No. 07/303,791 filed on Jan. 30, 1989, now abandoned, which is a division of U.S. patent application Ser. No. 07/045,459 filed on May 7, 1987, now U.S. Pat. No. 4,801,452, which is a continuation-in-part of U.S. patent application Ser. No. 07/043,888 filed on Apr. 29, 1987, now abandoned, which is a continuation of U.S. patent application Ser. No. 06/863,582 filed on May 15, 1986, now abandoned.

TECHNICAL FIELD

The present invention relates to a composition and method for lysing fibrin clots, dissolving thrombi, and reestablishing and maintaining perfusion of ischemic tissue. More particularly, the present invention relates to a composition comprising certain ethylene oxide-propylene oxide condensation products, which are surface-active copolymers, in combination with fibrinolytic enzymes.

BACKGROUND OF THE INVENTION

The term "fibrinolytic enzyme" means any enzyme that is capable of cleaving fibrin. Enzymes that are capable of cleaving fibrin include, but are not limited to, streptokinase, urokinase, tissue plasminogen activator (t-PA) produced from cell cultures, tissue plasminogen activator produced by recombinant DNA technology (rt-PA) and tissue plasminogen activator produced by prourokinase (k-PA). The terms "isotonic solution" or "isoosmotic solution" are defined as solutions having the same or similar osmotic pressure as blood. The terms clot, fibrin clot and thrombus are used interchangeably.

Each year about 550,000 Americans die from heart attacks. Even more—close to 700,000—have heart attacks and live. While a heart attack victim may survive, part of his or her heart will almost certainly die. The death of heart muscle, called myocardial infarction, is due to coronary artery thrombosis in 70-90% of the cases. When a thrombosis, or blood clot, occludes one of the arteries of the heart, it compromises the flow of blood to the surrounding muscle This deprives the muscle of oxygen and other nutrients. In the past, nothing could be done to reverse this process. The high technology devices in intensive care units mostly supported patients so they could live while a portion of their heart died.

Similar situations occur in many other tissues when the blood supply to the tissue is affected by a thrombus- or embolus. Stroke, deep vein thrombosis and pulmonary embolus are examples.

Another area where fibrinogen/fibrin plays a role is tumors. There is now strong evidence that fibrinogen-related proteins are localized in solid tumors. The anatomical distribution of fibrin in tumors varies depending on the tumor type. In carcinomas, fibrin is deposited in the tumor stroma and around tumor nests and may be particularly abundant toward the tumor periphery and at the tumor host interface. By contrast, fibrin is often less prominent in older, more central tumor stroma characterized by sclerotic collagen deposits. Fibrin may also be found between individual carcinoma cells. In some, but not all such cases, interepithelial fibrin deposits are related to zones of tumor necrosis; however, zones of tumor necrosis are not necessarily sites of fibrin deposition. Fibrin deposition in sacromas has been less carefully studied than that in carcinomas. In lymphomas, fibrin deposits may be observed between individual malignant tumor cells as well as between adjacent, apparently reactive benign lymphoid elements. Fibrin has been reported to appear in zones of tumor sclerosis, as in Hodgkin's disease. Research has indicated that the pattern and extent of fibrin deposition are characteristic for a given tumor. (See *Hemostasis and Thrombosis, Basic Principles and Clinical Practice*, "Abnormalities of Hemostasis in Malignancy", pp. 1145-1157, ed. by R. W. Colman, et al., J. B. Lippincott Company, 1987).

The lack of a uniform vascular supply to tumors can impede diagnostic and therapeutic procedures. For example, hypoxic tumors are less susceptible to many drugs and to radiation. Conventional drugs and new drugs, such as monoclonal antibody conjugates, are not effective unless they are delivered to tumor cells. Fibrin deposits that surround some types of tumors inhibit delivery of the drugs to the tumor. The blood supply of tumors is further compromised by other factors as well. Blood vessels in tumors are frequently small and tortuous. The hydrodynamic resistance of such channels further impedes the flow of blood to tumors.

A similar situation occurs for different reasons during crisis of sickle cell anemia. Sickled red blood cells partially occlude small vessels producing local hypoxia and acidosis. This induces additional red blood cells to become sickled. The result is a vicious circle known as "crisis". Therapy involves increasing flow and oxygenation in affected areas. Another therapy involves the combination of calcium channel blockers. The formation of fibrin frequently complicates sickle cell crisis.

It has been found that certain enzymes are able act on fibrin deposits to open clogged arteries. The enzymes which have been used successfully include streptokinase, urokinase, prourokinase, tissue plasminogen activator produced from cell cultures and tissue plasminogen activator produced by recombinant DNA technology. These enzymes are most successful if administered shortly after the occlusion of the blood vessels before the heart tissue has sustained irreversible damage. In one study of 11,806 patients treated with intravenous or intracoronary artery streptokinase, an 18% improvement of survival was demonstrated.

If the treatment was begun within one hour after the initial pain onset of the heart attack, the in-hospital mortality was reduced by 47%. (See *The Lancet*, Vol. 8478, p. 397-401, Feb. 22, 1986). It was demonstrated that early lysis of the thrombus resulted in salvage of a portion of heart tissue which would otherwise have died. In studies using angiography to assess the patency of blood vessels, it was found that tissue plasminogen activator could completely open the vessels of 61% of the 129 patients versus 29% of controls who were not treated with the enzyme. (See Verstraete, et al., *The Lancet*, Vol. 8462, p. 965-969), Nov. 2, 1985). Tissue plasminogen activator requires the addition of approximately 100 µl of Tween 80 per liter of solution to promote dispersion of the enzyme. (See Korninger, et al.,

*Thrombos, Haemostas*, (Stuttgart) Vol. 46(2), p. 561-565 (1981)).

The enzymes used to lyse thrombi in vessels do so by activating fibrinolysis. Fibrin is the protein produced by polymerization of fibrinogen. It forms a gel which holds the thrombus together. The fibrin molecules which form clots gradually become cross-linked to make a more stable clot. All four enzymes, prourokinase, urokinase, streptokinase and tissue plasminogen activator, have similar effects on fibrin; however, they have different toxicities. If the fibrinolysis mechanisms are activated in the vicinity of a clot, the clot is lysed. If, however, they are activated systemically throughout the circulation, the body's capacity to stop bleeding or hemorrhage is markedly reduced. Streptokinase and urokinase tend to activate systemic fibrinolysis. Consequently, they have been most effective when injected directly into the affected blood vessel. Tissue plasminogen activator, in contrast, becomes effective only when it is actually attached to fibrin. This means its activity is largely localized to the immediate area of a clot and does not produce systemic fibrinolysis. If high doses are used in an effort to increase the rate of clot lysis or to lyse refractory clots, then the amount of systemic fibrinolysis and risk of hemorrhage become significant. It can be injected intravenously into the general circulation. It circulates harmlessly until it contacts the fibrin in a blood clot where it becomes activated and lyses the clot. Tissue plasminogen activator is able to lyse a clot which is extensively cross-linked. This means it is possible to lyse clots which have been present for many hours. Tissue plasminogen activator also produces less risk of hemorrhage than the other enzymes. Even more effective enzyme based thrombolytic drugs are being developed.

Remarkable as the new enzyme therapies are, they are subject to serious complications and are not effective in all patients. Clots in the anterior descending branch of the left coronary artery are much more readily lysed than those in other arteries. If the enzyme is not delivered by the blood stream directly to the thrombus, it has no effect. For various reasons, more blood passes by or trickles around thrombi in the left anterior descending coronary artery than in the other major arteries. In addition, the presence of collateral circulation which forms in response to compromised blood flow in the major arteries adversely affects the rate of reopening or recanalization of the thrombosed major arteries. It is thought the presence of many collateral vessels which allows blood to bypass the clot reduces the pressure gradient across the clot. This in turn reduces the blood flow through the tiny openings which may persist in the clot, impedes the delivery of enzymes to the clot, and prevents it from being lysed.

Once the clot is lysed, the factors which led to the formation of the thrombus persist. This produces a high incidence of re-thrombosis and further infarction in the hours and days following lysis of the clot. Rethrombosis has been reported in between 3% and 30% of cases in which the initial treatment successfully lysed the clot. Anticoagulants are currently used to prevent the formation of new thrombi, but they tend to induce hemorrhage. There is a delicate balance between the amount of anticoagulation necessary to prevent re-thrombosis of the vessels and that which will produce serious hemorrhage.

Finally, dissolving the clot after irreversible damage has taken place has little effect. The irreversible damage could be either to the heart muscle or vascular bed of the tissue supplied by the blood vessel. A major problem in widespread implementation of this new enzyme therapy is to find ways of identifying and treating the patients earlier in their disease and to find ways to make the treatment effective for a longer period of time after the initiation of thrombosis.

Animal studies have provided a better understanding of the events which control blood flow and tissue death following coronary artery thrombosis. The heart has several blood vessels, so much of the muscle receives blood from more than one vessel. For this and other reasons, the tissue changes following a coronary thrombosis are divided into distinct zones. The central zone of tissue becomes almost completely necrotic. This is surrounded by an area of severe ischemia. Outside this is an area of lesser ischemia called the marginal zone. Finally, there is a jeopardized zone which surrounds the entire area. In studies with baboons, the central necrotic area was not affected by recanalization of the vessel after several hours. However, muscle in the other zones which had undergone less severe damage during the ischemic period could be salvaged. A surprising finding was that lysing of the thrombus to produce a perfect arteriograph was insufficient to restore normal flow in the majority of animals. (See Flameng, et al, *J. Clin. Invest.*, Vol. 75, p. 84-90, 1985).

Some further impediment to flow had developed in the area supplied by the vessel during the time that it was occluded. In further studies, it was demonstrated that immediately after removing the obstruction to the vessel, the flow through the damaged tissue began at a high rate. However, within a short time the blood flow through the ischemic zone decreased and the tissue died. Consequently, the regional blood flow immediately after reperfusion is a poor predictor of the salvage of myocardial tissue. If the blood flow through the damaged tissue remained near the normal levels, the success of tissue salvage was much greater. Hemmorhage occurred almost exclusively in the severely ischemic zone reflecting damage to the small blood vessels. The hemorrhage, however, remained limited to the severely ischemic tissue and did not cause extension of the infarction or other serious complication. Therapies which could preserve the blood flow through the small blood vessels distal to the major area of thrombus after reperfusion could be expected to markedly increase the salvage of myocardial tissue.

The damage to heart muscle cells which occurs after lysing the thrombus is due to other factors as well as ischemia. Contact of fresh blood with damaged or dead cells induces the influx of neutrophils, or pus cells, which kill heart cells which would otherwise have recovered. Much of the damage caused by neutrophils has been attributed to superoxide ions. The superoxide anion can damage tissue in several ways. The interaction of the superoxide anion with hydrogen peroxide leads to the production of hydroxyl radicals which are potentially toxic and react rapidly with most organic molecules. Mannitol is a selective scavenger of hydroxyl radicals. The enzyme, superoxide dismutase, catalyzes the decomposition of the superoxide anion. Enzymes such as superoxide dismutase, free radical scavengers or agents which prevent the influx on neutrophils are able to increase the salvage of heart muscle cells.

Low concentrations of copolymers have little effect on plasma proteins. Higher concentrations, above the critical micelle concentration, activate complement via the alternate pathway. This provides further benefit for treating heart attacks because the systemic activation of complement causes the neutrophils to become unresponsive to complement chemotaxis. This prevents their migration into the heart tissue.

Continuing therapy is needed even after restoration of blood flow and salvage of damaged tissue. The arteriosclerosis that caused the original heart attack remains. American and European researchers have found that arteriosclerosis still narrows the arteries in 70-80% of patients whose clots were lysed by thrombolytic therapy. Many physicians believe this obstruction must be opened for long term benefits. Balloon angioplasty is a procedure whereby a catheter with a small balloon is inserted into the narrowed artery. The balloon is inflated, compresses the atherosclerotic plaque against the vessel wall and dilates the artery. The effectiveness of this procedure is limited by the effects of ischemia produced by the balloon, by embolization of atheromatous material which lodges in distal vessels and by an increased tendency for immediate or delayed thrombosis in the area damaged by the balloon. The balloon tears the tissue exposing underlying collagen and lipid substances which induce formation of thrombi. The thrombus may occlude the vessel immediately or set up a sequence of events which leads to occlusion many days or weeks later. What is needed is a means of rendering the surface of the dilated vessel less thrombogenic, improving the blood flow through the distal tissue and breaking the embolized material into smaller pieces which are less likely to produce embolic damage.

Finally, lipid material on the atherosclerotic wall contributes to the bulk of the plaque which narrows the lumen of the artery and produces a highly thrombogenic surface. What is needed is a method of extracting or covering lipids from atherosclerotic plaques which leaves their surfaces less thrombogenic and reduces their bulk.

Use of copolymers prepared by the condensation of ethylene oxide and propylene oxide to treat an embolus or a thrombus has been described (See U.S. Pat. No. 3,641,240). However, the effect was limited to recently formed, small (preferably microscopic) thrombi and emboli which are composed primarily of platelets. The use of the ethylene oxide and propylene oxide copolymer has little or no effect on a clot in a patient who has suffered a severe coronary infarction. The clots that form in these patients are large and stable clots. Stable clots are clots in which the fibrin that has formed from fibrinogen has undergone cross linking. Fibrin which has undergone crosslinking is not effected by presence of the ethylene oxide-propylene oxide copolymers. The copolymers only affect new clots in which the newly formed fibrin has not crosslinked.

Thus, a composition is needed that is capable of lysing a clot and, at the same time, will prevent a second clot from reforming after the initial clot has been cleared. Ideally, such a composition would also reduce as much as possible any damage that is caused by blockage of blood supply to the tissue. Such a composition would thereby protect the patient from any damage caused by the reformation of a clot. In addition, such a composition would be useful in removing clots from solid tumors, increasing flow through tortuous channels and thereby allow delivery of therapeutic drugs to the tumor.

SUMMARY OF THE INVENTION

In accordance with the present invention, a composition is provided that is effective in dissolving blood clots and reestablishing and maintaining blood flow through thrombosed coronary or other blood vessels. The fibrinolytic composition of the present invention comprises an enzyme, such as streptokinase, urokinase, prourokinase, tissue plasminogen activator, or other fibrinolytic enzyme, and a surface-active copolymer. The surface-active copolymer can be an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably about 1750 to 3500, and b is an integer such that the hydrophile portion represented by $(C_2H_4O)$ constitutes approximately 50% to 90% by weight of the compound.

The fibrinolytic composition of the present invention is usually administered by intravenous injection into a patient.

The present invention provides a composition that can be administered to patients who have a blood clot occluding a blood vessel. The combination of fibrinolytic enzyme and surface-active copolymer according to the present invention increases blood flow around a clot, rapidly lyses a clot, and provides further protection to the patient by preventing a new clot from forming and reducing reperfusion injury.

Another embodiment of the present invention is the combination of the surface-active copolymer and oxygen radical scavengers such as superoxide dismutase and mannitol. The present invention includes the combination of surface-active copolymer, clot lysing enzyme and free radical scavenger and also the combination of surface-active copolymer and free radical scavenger alone.

Because the fibrinolytic composition of the present invention stabilizes the patient to a greater extent than treatments in the prior art, the administration of more invasive procedures, such as balloon angioplasty, can be delayed thereby permitting selection of conditions for the invasive treatment that are most favorable to the patient.

Another embodiment of the present invention is the use of the surface-active copolymer to treat sickle cell disease. Yet another embodiment of the present invention is the use of the surface-active copolymer to preserve organs for transplantation.

Accordingly it is an object of the present invention to provide a combination of fibrinolytic enzymes with a surface-active copolymer to produce a synergistic action in lysing blood clots. This combination can be formulated either with standard doses of enzyme to increase the rate or likelihood of lysing a clot or at lower doses of enzyme to reduce side effects while maintaining efficacy for lysing clots.

It is another object of the present invention to provide a composition that will reduce the need for anticoagulation in cardiac therapy and thereby lessen the danger of hemorrhage.

It is another object of the present invention to provide a composition that accelerates the dissolution of clots by freeing aggregated platelets and blocking further platelets from aggregating to the clot.

It is yet another object of the present invention to provide a composition that can reduce the dose of fibrinolytic enzyme required to lyse a clot and thereby reduce the incidence of complications.

It is another object of the present invention to provide a composition that contains a surface-active copolymer and a free radical or oxygen scavenger, such as superoxide dismutase or mannitol.

It is a further object of the present invention to provide a composition that can promote blood flow through microvascular channels of tissue damaged by ischemia and reduce the amount of tissue which undergoes necrosis.

It is a further object of the present invention to provide a composition that will significantly reduce the risk of rethrombosis after treatment with fibrinolytic enzymes.

It is a further object of the present invention to provide a composition that will promote removal of lipids from atherosclerotic vessel walls and thereby lessen the incidence of rethrombosis.

It is another object of the present invention to provide an improved fibrinolytic composition that is capable of lysing fibrin deposits associated with tumors.

It is another object of the present invention to provide a composition which will increase blood flow through tortuous channels such as occur in tumors and during crisis of sickle cell disease.

It is another object of the present invention to provide an improved composition and method for ex vivo preservation of organs.

It is another object of the present invention to provide a composition that will reduce the risk of rethrombosis and thereby allow delay in administering balloon angioplasty or other invasive procedures for treatment of the compromised vessels.

It is another object of the present invention to provide a composition which will reduce the risk of thrombosis immediately or at some time after invasive procedures such as balloon angioplasty which damage endothelial cells of the vasculature.

It is a further object of the present invention to provide a composition to block the aggregation of platelets in blood vessels distal to the thrombosis and thereby limit extension of tissue damage.

It is yet another object of the present invention to provide a composition to improve blood flow through and around tissue with extensive necrosis of myocardial or other cells thereby retarding necrosis of additional myocardial tissue.

It is another object of the present invention to provide a composition which will reduce the influx of neutrophils into damaged tissue and thereby reduce the extent of injury caused by toxic products of neutrophils.

It is yet another object of the present invention to provide a composition that will decrease the amount of ischemia caused blockage of blood flow by a thrombus.

It is a further object of the present invention to provide a combination of a thrombolytic enzyme, balloon angioplasty or other operative procedures and a surface-active copolymer to produce an improved method of removing a thrombus or thrombogenic occlusion and reducing obstructive conditions which promote rethrombosis.

It is another object of the present invention to provide a composition and method for the treatment of crisis in sickle cell disease.

These and other objects, features and advantages of the present invention will become apparent after a review of the following detailed description of the disclosed embodiment and the appended claims.

DETAILED DESCRIPTION OF THE DISCLOSED EMBODIMENT

The present invention comprises a composition which provides a synergistic action in lysing blood clots and reestablishing and maintaining blood flow through a thrombosed cornorary vessel or other blood vessel. The fibrinolytic composition of the present invention is a solution containing an effective concentration of a fibrinolytic enzyme and an effective concentration of a surface-active copolymer. The combination of the two components is effective in dissolving blood clots that are blocking blood vessels. In addition, the fibrinolytic composition of the present invention is highly effective in preventing a blood clot from reforming and in maintaining blood flow through the blood vessel and affected ischemic tissue.

The fibrinolytic composition of the present invention improves the flow of blood through narrow channels around clots and increases the delivery of the fibrinolytic enzyme to the clot. The present invention also speeds the rate of dissolution of the clot by the enzyme and increases the proportion of clots lysed by promoting delivery of enzyme to clots which would not otherwise be exposed to sufficient enzyme for their dissolution. In addition, the fibrinolytic composition of the present invention reduces the dose of enzyme required for particular applications and thereby reduces the incidence of complications due to side effects caused by the enzymes.

The fibrinolytic composition of the present invention reduces the risk of immediate rethrombosis by accelerating the dissolution of clots, freeing aggregated platelets and blocking further platelets from aggregating to the clot or clot site. By reducing the risk of immediate rethrombosis, the fibrinolytic composition of the present invention will allow delay of a balloon angioplasty or other invasive procedures for treatment of the comprises vessels which have become thrombosed. The delay will permit selection of conditions for invasive treatment most favorable to the patient.

Solutions which may be employed in the preparation of the fibrinolytic composition of the present invention include, but are not limited to, saline (a solution of sodium chloride, containing 8.5 to 9.5 grams of sodium chloride in 1000 cc of purified water), Ringer's solution, lactated Ringer's solution, Krebs-Ringer's solution, and various sugar solutions. All of these solutions are well known to one of ordinary skill in the art. However, it is to be understood that the fibrinolytic composition of the present invention may be administered as a solution that is not isotonic.

The surface-active copolymer is preferably an ethylene oxide-propylene oxide condensation product with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably from 1750 to 3500, and b is an integer such that the hydrophile portion represented by $(C_2H_4O)$ constitutes from about 50% to 90% by weight of the compound. These copolymers are sold under the general trademark of Pluronic ® polyols and are available from the BASF Corporation (Parsippany, N.J.).

The surface-active copolymers of the present invention are not metabolized by the body and are quickly eliminated from the blood. The half-life of the copolymer in the blood is approximately two hours. It is to be understood that the surface-active copolymer in the improved fibrinolytic composition of the present invention is not covalently bound to any of the other components in the composition.

The polymer blocks are formed by condensation of ethylene oxide and propylene oxide at elevated temperature and pressure in the presence of a basic catalyst. There is some statistical variation in the number of monomer units which combine to form a polymer chain in each copolymer. The molecular weights given are approximations of the average weight of copolymer molecule in each preparation. It is to be understood that the blocks of propylene oxide and ethylene oxide do not have to be pure. Small amounts of other materials can be admixed so long as the overall physical chemical properties are not substantially changed. A more detailed discussion of the preparation of these products is found in U.S. Pat. No. 2,674,619 which is incorporated herein by reference.

Illustrative ethylene oxide-propylene oxide condensation products which may be employed in the preparation of the fibrinolytic composition of the present invention include, but are not limited to, the following copolymers:

1. A polyol with an average molecular weight of 4700 containing approximately 80% by weight ethylene oxide.
2. A polyol with an average molecular weight of 3400 containing approximately 50% by weight ethylene oxide.
3. A polyol with an average molecular weight of 7700 containing approximately 70% by weight ethylene oxide.
4. A polyol with an average molecular weight of 14,600 containing approximately 80% by weight ethylene oxide.
5. A polyol with an average molecular weight of 12,600 containing approximately 70% by weight ethylene oxide.
6. A polyol with an average molecular weight of 9500 containing approximately 90% by weight ethylene oxide.

The preferred ethylene oxide-propylene oxide copolymer for use in the fibrinolytic composition of the present invention is a copolymer having the following formula:

$$HO(C_2H_4O)_b(C_3H_6O)_a(C_2H_4O)_bH$$

wherein the molecular weight of the hydrophobe $(C_3H_6O)$ is approximately 1750 and the total molecular weight of the compound is approximately 8400.

The concentration of copolymer in the clot-dissolving composition of the present invention can vary depending the total volume of solution needed in the particular circumstances. The total amount of block copolymer employed in the present invention will also vary depending on the size and type of thrombus or embolus, the particular copolymer employed, the particular fibrinolytic enzyme employed, and the size and weight of the patient.

The copolymer can be used over a wide range of concentrations with no adverse side effects. The copolymer is rapidly excreted intact; as much as 90% of the copolymer administered is excreted in as little as three hours. Because of its low toxicity and the rapid clearance from the body, the copolymer can be administered over a long period of time.

The fibrinolytic composition of the present invention may be employed by admixing with blood in any standard manner. Preferably, however, the solutions are intravenously injected into the blood stream either as a bolus, slow drip or both. The solutions are generally admixed with the blood in a manner so as to maintain a substantially steady venous pressure.

It is to be understood that separate administration of a solution of the surface-active copolymer and a fibrinolytic enzyme are contemplated in the present invention. For example, a solution of the surface-active copolymer and a solution of a fibrinolytic enzyme could be prepared separately and administered simultaneously or sequentially to a patient suffering from a thrombus blocking a coronary artery. Simultaneous or sequential administration of the two components (copolymer and fibrinolytic enzyme) of the fibrinolytic composition of the present invention has the same effect as administering the components together and is therefore contemplated in the present invention.

The fibrinolytic enzymes that can be used in the fibrinolytic composition of the present invention include, but are not limited to, streptokinase (available from Hoechst-Roussel under the trademark Streptase ®), urokinase (available from Abbot Laboratories, North Chicago, Ill. under the trademark Abbokinase ®) and tissue plasminogen activator (Biopool AB, Umeå, Sweden). The tissue plasminogen activator can be derived from eukaryotic cells such as human melanoma cells or can be made by genetic engineering methods such as recombinant DNA. Some of the fibrinolytic enzymes are only sparingly soluble in water and must therefore be emulsified with the surface-active copolymer before administration to the patient.

Ideally, a bolus injection of the copolymer solution without the enzyme is administered before the present invention is administered. For example, a 3% solution of the copolymer in 5% isotonic dextrose is injected within a two minute period so that the blood concentration of copolymer is approximately 0.6 mg/ml. In addition, it can be advantageous to administer a solution of the copolymer by intravenous drip at a rate of about 25 mg/kg body weight/hour to obtain of blood concentration of the copolymer of approximately 0.6 mg/ml for up to four days or longer following the administration of the fibrinolytic composition of the present invention. This treatment will aid in preventing a clot from re-forming.

Although the descriptions relate mostly to heart disease, it is to be understood that the fibrinolytic composition of the present invention is equally applicable to thrombosis in other parts of the body, such as the brain, legs, lungs or gastrointestinal tract.

The present invention includes a method for dissolving clots in blood vessels comprising the steps of injecting into a body a solution with an effective concentration of a surface-active copolymer with the following formula:

$$HO(C_2H_4O)_b(C_3H_6O)_a(C_2H_4O)_bH$$

wherein a is an integer such that the hydrophobe represented by $(C_3H_6O)$ has a molecular weight of from 950 to 4000, preferably from 1750 to 4000, and b is an integer such that the hydrophile portion represented by $(C_2H_4O)$ constitutes from approximately 50% to 90% by weight of the compound. The blood concentration of the surface active copolymer is between approximately 0.1 mg/ml and 6 mg/ml, preferably between 0.5 mg/ml and 2 mg/ml. A solution with an effective concentration of a fibrinolytic enzyme and an effective amount of the surface-active copolymer is then injected into the body. After the clot is dissolved or lysed, a solution with an effective concentration of the surface-active copolymer is then injected into the body. The concentration of the copolymer is maintained between approximately 0.4 and 2 mg/ml of blood for between approximately 4 hours and 144 hours.

The present invention also includes a method of removing fibrin from a tumor comprising the step of injecting into a body a solution with a clot dissolving composition, said composition comprising an effective amount of a fibrinolytic enzyme and an effective amount of a surface-active copolymer of the following formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably from 1750 to 4000, and b is an integer such that the hydrophile portion represented by $(C_2H_4O)$ constitutes from approximately 50% to 90% by weight of the compound. The fibrinolytic composition of the present invention can be administered directly to the tumor.

Removal of the fibrin from the tumor increases the accessibility of diagnostic reagents to the tumor. The method also increases the accessibility and sensitivity of the tumor to the chemotherapy.

The present invention includes a method of improving blood flow and oxygenation of a tumor comprising the step of injecting into a body a solution comprising an effective concentration of a surface-active copolymer of the following formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably from 1750 to 4000, and b is an integer such that the hydrophile portion represented by $(C_2H_4O)$ constitutes from approximately 50% to 90% by weight of the compound.

The present invention also includes an improved ex vivo tissue perfusion composition comprising blood, a solution with an effective amount of an anticoagulant, and an effective amount of a surface-active copolymer of the following formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably from 1750 to 4000, and b is an integer such that the hydrophile portion represented by $(C_2H_4O)$ constitutes from approximately 50% to 90% by weight of the compound. The ex vivo tissue perfusion composition can be diluted with a colloidal solution or a salt solution. The preferred anticoagulant is heparin. This embodiment of the present invention is useful in prolonging the life of human or animal organs that are to be used in transplantation.

The present invention also includes a method of treating sickle cell disease comprising the step of injecting into a body a solution with a fibrinolytic composition therein, the composition comprising an effective concentration of a fibrinolytic enzyme and an effective amount of a surface-active copolymer of the following formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably from 1750 to 4000, and b is an integer such that the hydrophile portion represented by $(C_2H_4O)$ constitutes from approximately 50% to 90% by weight of the compound.

The present invention includes a method of treating sickle cell disease comprising the step of injecting into a body a solution comprising an effective concentration of a surface-active copolymer of the following formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000, preferably from 1750 to 4000, and b is an integer such that the hydrophile portion represented by $(C_2H_4O)$ constitutes from approximately 50% to 90% by weight of the compound.

The following specific examples will illustrate the invention as it applies in particular to dissolving clots in blood vessels and to preventing clots from reforming. It will be appreciated that other examples will be apparent to those of ordinary skill in the art and that the invention is not limited to these specific illustrative examples.

EXAMPLE I

Addition of the copolymer to a clot dissolving enzyme results in a synergistic effect on the clot dissolving activity of the enzyme as demonstrated in this Example.

Sterile 1 ml tuberculin syringes are packed with 0.6 ml of 500 to 750 micron glass beads (Polyscience, Inc., Warington, Pa.). The tips of the syringes are plugged with nytex filters and a one-way plastic stopcock. Fresh frozen platelet-poor citrated plasma is spiked with 15 $\mu$Ci/ml $^{125}$I human fibrinogen (Sigma Chemical Co., St. Louis, Mo.). The radioactive plasma is diluted 1:2 with normal saline, and recalcified with calcium (American Dade, Aquada, Puerto Rico) at 1 volume of calcium to 4 volumes diluted plasma.

Radioactive fibrinogen is bound to the glass bead columns as follows: Equal volumes of the radioactivily labelled recalcified plasma are added to parallel bead columns and allowed to run through the beads with no excess plasma above the beads. All procedures and manipulations of the "bead clots" are performed at 37°

C. The bead/plasma clots are allowed to incubated for 30 minutes, then washed for 30 minutes with normal saline. During the last 5 minutes of the wash with saline, the flow rates are monitored and columns whose flow rates are abnormally fast or slow are excluded from the experiment. Normal flow rates average 0.2 ml/minute.

The copolymer that is used in this example has the following formula:

wherein the molecular weight of the hydrophole ($C_3H_6O$) is approximately 1750 and the total molecular weight of the compound is approximately 8400. The copolymer is prepared as a stock solution of 1% copolymer by weight in normal saline.

Blood containing t-PA, with or without the copolymer, is passed through the columns as follows: 10 ml of heparinized whole blood is drawn fresh and mixed with t-PA (10 μg in 1 ml normal saline; single chain; Sigma Chemical Co. St. Louis, Mo.). A volume of 5.5 ml of blood is mixed with either 0.5 ml normal saline or 0.5 ml of copolymer stock solution. One aliquot of a preparation of whole blood or whole blood diluted 1:3 with normal saline is run on each column. Three ml of each blood preparation is added to a reservoir connected to each column. Fractions are collected every minute until all flow ceased. The volume in each tube is measured and radioactivity counted in a Tracor Analytic gamma counter (TmAnalytic, Inc., Elk Grove Village, Ill.) Appearance of radioactivity in the collection tubes indicates lysis of the clot.

Figure 1:
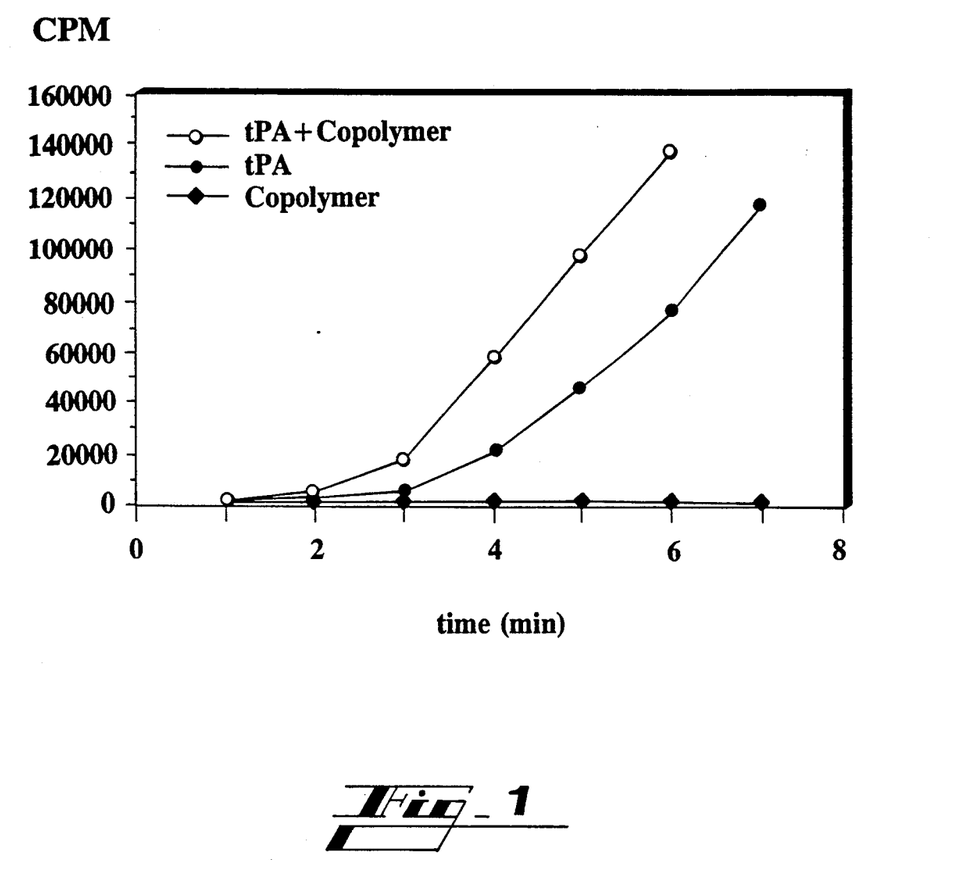
FIG. 1 is a diagram showing cumulative $^{125}I$ fibriogen (counts per minute) released from the columns potted as a function of time.

The data are summarized in Table A and FIG. 1. FIG. 1 shows cumulative $^{125}I$ fibrinogen (counts per minute) released from the columns plotted as a function of time.

TABLE A

| Perfusate* | Time (Minutes) | Volume Recovered | Counts Minute (Volume) | Counts Minute (ml) | Counts Minute (Cumulative) |
|---|---|---|---|---|---|
| Blood, t-PA, Copolymer | 1 | 0.3 | 2031 | 6770 | 2031 |
|  | 2 | 0.25 | 3042 | 12168 | 5073 |
|  | 3 | 0.3 | 13051 | 43503 | 18124 |
|  | 4 | 0.2 | 40190 | 200950 | 58314 |
|  | 5 | 0.25 | 40260 | 161040 | 98574 |
|  | 6 | 0.25 | 40009 | 160036 | 138583 |
| Blood, t-PA | 1 | 0.15 | 885 | 5900 | 885 |
|  | 2 | 0.2 | 1330 | 6650 | 2215 |
|  | 3 | 0.2 | 3681 | 18405 | 5896 |
|  | 4 | 0.3 | 16333 | 54443 | 22229 |
|  | 5 | 0.4 | 24932 | 62330 | 47161 |
|  | 6 | 0.45 | 30545 | 67878 | 77706 |
|  | 7 | 0.6 | 40365 | 67275 | 118071 |
| Blood, Copolymer | 2 | 0.8 | 340 | 425 | 340 |
|  | 3 | 0.7 | 351 | 501 | 691 |
|  | 4 | 0.6 | 270 | 450 | 961 |
|  | 5 | 0.6 | 226 | 377 | 1187 |
|  | 6 | 0.5 | 204 | 408 | 1391 |
|  | 7 | 0.4 | 178 | 445 | 1569 |

*A simulated thrombus containing $^{125}I$ fibrin is prepared as described in the text. The ability of test preparations to dissolve the fibrin is determined by measuring the rate of elution of radioactivity from the column. The copolymer is not an enzyme and has no reactive groups, so it is unable to lyse cross-linked fibrin, but it does increase the fibrinolytic activity of t-PA in this model which is designed to simulate the structure and flow conditions of a coronary thrombus.

As can be seen from Table A and FIG. 1, treatment of the radioactive clot with the surface-active copolymer releases little of the radioactivity indicating no lysis of the clot. Administration of t-PA to the clot causes release of radioactivity indicating lysis of the clot in the column. However, when the surface-active copolymer is added to the solution, the rate of lysis of the clot in the column is dramatically increased. Thus, the combination of surface-active polymer and t-PA lysed the clot in the column at a significantly faster rate than did t-PA alone.

In other experiments, the model is modified by changing the size of the beads, the concentration of plasma used to make the clot, the dilution of blood or the concentration of enzyme or copolymer. In several instances, columns are produced in which whole blood fails to flow at all while blood with copolymer flows at a rate of about 0.05 ml/minute. t-PA in the blood is unable to dissolve any of the fibrin in such clots as measured by release of $^{125}I$ label because there is no flow of blood through the clot. The use of copolymer with the blood and t-PA in such situations caused rapid lysis of the clot.

EXAMPLE II

The fibrinolytic composition is tested in an ex vivo rat heart model. The detailed design of the system is described elsewhere. (See Paulson, et al., Basic Res. Cardiol., Vol. 81, pp. 180-187, 1986 which is incorporated herein by reference). This model measures the ability of the isolated heart to recover from a 30 to 90 minute ischemic period where the flow of nutrients is reduced to 1 percent of normal or completely stopped, then followed by a 10 minute period of reperfusion. Three parameters measured: (1) cardiac output (CO); (2) left ventricular systolic pressure (LVSP); and (3) left ventricular contraction (dp/dt). Assessment of heart recovery and amount of damage are discussed in Paulson, D. J. et al. Basic Res. Cardiol., Vol. 79, pp. 551-561, 1984.

In this experiment, hearts are perfused with washed whole human blood with no heparin added. Flow is completely stopped for 30 minutes, followed by 10 minutes reperfusion with washed whole human blood without heparin but with the additive or additives indicated in Table B. The copolymer that is used in this example has the following formula:

wherein the molecular weight of the hydrophobe ($C_3H_6O$) is approximately 1750 and the total molecular weight of the compound is approximately 8400. The copolymer is prepared as a stock solution of 1% copolymer by weight in normal saline.

The results of the test are as follows. The final concentration of the surface-active copolymer used in this Example is 0.68 mg/ml. The streptokinase that is used in this Example can be obtained from Sigma Chemical Company, St. Louis, Mo. Streptokinase is administered at a concentration of 100 units/heart. The result are shown in Table B.

TABLE B

| Additions | Percent Cardiac Recovery (Values are mean) | | |
|---|---|---|---|
|  | CO | LVSP | dp/dt |
| Whole Blood | 5 | 24 | 10 |
| with Copolymer | 38 | 82 | 65 |
| with Streptokinase | 33 | 75 | 60 |
| with Copolymer and Streptokinase | 58* | 88 | 78 |

*$p < 0.05$ for cardiac output (CO) differences between the combination of Copolymer and Streptokinase and (a) whole blood ischemic control, (b) Copolymer only, and (c) Streptokinase only. Student's t test was used to determine differences between independent means. A result of $p < 0.05$ was regarded as significant.

As can be seen from Table B, the copolymer and streptokinase combination clearly protected the heart better than the copolymer or streptokinase alone.

EXAMPLE III

For treating a patient weighing about 180 lbs with a pulmonary embolism, reconstitute 500 mg of urokinase (Abbokinase, Abbot Laboratories, North Chicago, Ill.) in 105 ml of sterile water. To the urokinase solution add 90 ml of an 0.9% sodium chloride solution containing 6.0 grams of an ethylene oxide-propylene oxide copolymer with the following formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is approximately 8400. The urokinase and the copolymer are thoroughly mixed to form a homogeneous solution. The final volume of the solution is 195 ml.

Administer the fibrinolytic composition of the present invention by means of a constant infusion pump that is capable of delivering a total volume of 195 ml. A priming dose of the fibrinolytic composition of the present invention is administered at a rate of 90 ml/hour over a period of 10 minutes. This is followed by a continuous infusion of the present invention at a rate of 15 ml/hour for 12 hours. Because some of the fibrinolytic composition of the present invention will remain in the tubing at the end of an infusion pump delivery cycle, the remaining solution is flushed out of the tube by administering a solution of 0.9% sodium chloride at a rate of 15 ml/hour.

EXAMPLE IV

For treating a patient with a coronary artery thrombi, reconstitute 75 mg of urokinase (Abbokinase, Abbot Laboratories, North Chicago, Ill.) in 15.6 ml of sterile water. To the urokinase solution add 300 ml of 5% dextrose solution containing 15 grams of an ethylene oxide-propylene oxide copolymer with the following formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is approximately 8400. The urokinase and the copolymer are thoroughly mixed to form a homogeneous solution. The solution is then diluted with 5% dextrose to a final volume of 500 ml.

The solution comprising the present invention is infused into the occluded artery at a rate of 4 ml per minute for periods up to 2 hours. To determine response to the solution of the fibrinolytic composition of the present invention, periodic angiography is performed.

EXAMPLE V

For treating a patient weighing about 180 lbs with a pulmonary embolism, reconstitute 500 mg of urokinase (Abbokinase, Abbot Laboratories, North Chicago, Ill.) in 105 ml of sterile water. To the urokinase solution add 90 ml of an 0.9% sodium chloride solution containing 6.0 grams of an ethylene oxide-propylene oxide copolymer with the following formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is approximately 8400. The urokinase and the copolymer are thoroughly mixed to form a homogeneous solution. The solution is then diluted with 0.9% sodium chloride to a final volume of 195 ml.

Administer 137 ml of a 5% isotonic dextrose solution with 3% wt/vol ethylene oxide-propylene oxide copolymer lysed therein to the patient over a 2 minute period. This gives a blood concentration of copolymer of approximately 0.6 mg/ml (assuming blood is 8% of body weight)

The fibrinolytic composition of the present invention is then immediately administered by means of a constant infusion pump that is capable of delivering a total volume of 195 ml. A priming dose of the present invention is administered at a rate of 90 ml/hour over a period of 10 minutes. This is followed by a continuous infusion of the present invention at a rate of 15 ml/hour for 12 hours. Because some of the present invention will remain in the tubing at the end of an infusion pump delivery cycle, the remaining solution is flushed out of the tube by administering a solution of 0.9% sodium chloride containing 3.0% copolymer at a rate of 15 ml/hour.

After the clot is lysed, a solution of the copolymer is administered by intravenous drip at a rate of about 25 mg/kg body weight/hour to maintain a blood concentration of the copolymer of approximately 0.6 mg/ml. The administration of the copolymer solution is continued for four days following the administration of the fibrinolytic composition of the present invention.

EXAMPLE VI

For ex vivo organ preservation in preparation for transplantation, reconstitute 1000 units of heparin (Sigma Chemical Company, St. Louis, Mo.) in 200 ml of normal (0.9%) sodium chloride solution and add 1.36 g of the copolymer of the present invention and resuspend washed whole human blood to formulate the perfusion medium. The copolymer has the following formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is 8400.

Hearts excised from anesthetized Sprague-Dawley rats were perfused for 10 minutes with (a) blood and heparin or with (b) blood, heparin and copolymer following a 90 minute low-flow ischemia. Cardiac output (CO), left ventricular systolic pressure (LVSP) and left ventricular contraction (dp/dt) were determined and are expressed as percent of recovery as compared to normal hearts. Ischemic animals' hearts which received blood with heparin showed poor recovery: 12% CO, 44% LVSP and 34% dp/dt. Hearts given blood, heparin and copolymer showed excellent recovery: 90% CO, 92% LVSP, and 84% dp/dt. For the heparin with copolymer group, all three parameters were statistically different (p<0.01) as compared to the ischemic control group (heparin only). Differences between independent means were determined by the Student's t test.

EXAMPLE VII

A test is performed to demonstrate the ability of the combination of superoxide dismutase and an appropriate copolymer to produce greater protection of ischemic myocardium from reperfusion injury associated with oxygen radicals and other factors than superoxide dismutase alone.

Under general anesthesia (sodium thiopental 25 mg/kg), the animals are intubated and ventilated with 70% oxygen at a rate of 12 breaths per minute. A satisfactory level of anesthesia is maintained with intermittent boluses of pentothal as required. After skin preparation, a left anterior thoracotomy is performed, the pericardium incised and the heart exposed. The left anterior descending coronary artery is identified, isolated and encircled with a snare 1 cm from its origin. Temporary left anterior descending coronary artery occlusion is accomplished by tightening the snare and continues for 90 minutes. During the procedure, the heart rate and blood pressure are monitored utilizing a Hewlett-Packard 7758B 8-channel recorder. Arterial blood pressure is monitored through an 18 gauge indwelling catheter in the right femoral artery and measured with a Hewlett-Packard quartz transducer. Electrocardiographic evidence for anteroseptal myocardial ischemia is also monitored. Reperfusion of the ligated vessel after 90 minutes of ischemia is achieved by a gradual release of the snare to prevent the hyperemic response. A defibrillator is available in the room as are all necessary cardiotonic drugs in the event of cardiac fibrillation or circulatory collapse due to the left anterior descending coronary artery ligation. Therapeutic agents are infused in conjunction with reperfusion as follows: bovine superoxide dismutase with approximately 3000 units of activity per milligram assayed by the method of McCord, *J. Biol. Chem.*, Vol. 244, p. 6049 (1969) is obtained from Sigma Chemical Company, St. Louis, Mo. It is dissolved in 100 ml of normal saline and infused intravenously over 90 minutes starting 15 minutes before restoration of perfusion. This simulates the effects which occur during lysis of a coronary thrombus.

A solution of copolymer is prepared at 2% weight/volume in saline. It is given intravenously as a bolus over 2 minutes in a dose sufficient to achieve a blood level of 0.6 mg/ml followed by a constant infusion of approximately 25 mg/kg/hour in order to maintain the blood level of approximately 0.6 mg/ml for the remainder of the experiment.

The ethylene oxide-propylene oxide copolymer has the following general formula:

wherein the molecular weight of the hydrophobe ($C_3H_6O$) is approximately 1750 and the total molecular weight of the compound is 8400.

The synergistic effect of the combination is demonstrated by comparing the results of dogs treated with both the copolymer and superoxide dismutase with those treated with either material alone or no treatment.

Agents are infused intravenously utilizing an IVAC 560 infusion pump. Infusion begins 15 minutes prior to release of the snare and continues until the total dose for each group has been administered. The chest is closed is layers. A chest tube is utilized to evacuate the pneumothorax and is removed when spontaneous respirations resume. Intravenous fluids are given (Lactated Ringer's Solution) to compensate for the 24 hour NPO period preceding the operation, in addition to a 3 to 1 ratio to compensate for blood loss. The animals are then maintained and followed closely for the next 24 hours. Each animal is then returned to the operating suite and under general anesthesia the previous incision is reopened. The animal is sacrificed utilizing a barbiturate overdose. The heart and proximal 4 cm of ascending aorta is excised being sure to include the origins of the coronary arteries.

All groups are subjected to the same procedures for identification of the area of the myocardium at risk for infarction and the area actually infarcted.

This technique involves perfusion of the left anterior descending coronary artery with 2, 3, 5-triphenyltetrazolium chloride, which stains the intact myocardium red and leaves the infarcted myocardium unstained. The limits of the area of myocardium at risk are determined by perfusing the remainder of the coronary system, via the aortic root, with Evans Blue dye. The area at risk is defined by a lack of Evans Blue stain.

It should be understood, of course, that the foregoing relates only to a preferred embodiment of the present invention and that numerous modifications or alterations may be made therein without departing from the spirit and the scope of the invention as set forth in the appended claims.

We claim:

1. An organ perfusion composition containing a solution of:

a perfusion medium; and an effective amount of a surface-active copolymer dissolved in the perfusion medium, the surface-active copolymer having the following formula:

$$HO(C_2H_4O)_b(C_3H_6O)_a(C_2H_4O)_bH$$

wherein a is an integer such that the hydrophobe represented by ($C_3H_6O$) has a molecular weight of approximately 950 to 4000, and b is an integer such that the hydrophile portion represented by ($C_2H_4O$) constitutes approximately 50% to 90% by weight of the compound.

2. The composition of claim 1, wherein said surface-active copolymer has the following formula:

wherein a is an integer such that the hydrophobe represented by ($C_3H_6O$) has a molecular weight of approximately 1200 to 3500, and b is an integer such that the hydrophile portion represented by ($C_2H_4O$) constitutes approximately 50% to 90% by weight of the compound.

3. The composition of claim 1, wherein said surface-active copolymer has the following formula:

wherein the molecular weight of the hydrophobe ($C_3H_6O$) is approximately 1750 and the total molecular weight of the compound is approximately 8400.

4. The composition of claim 1, wherein the perfusion medium is blood.

5. The composition of claim 1, wherein the perfusion medium is a balanced salt solution.

6. A method of perfusing an organ comprising the step of perfusing the organ with a composition comprising a perfusion medium with a surface-active copolymer dissolved in the perfusion medium, the surface-active copolymer having the following formula:

$$HO(C_2H_4O)_b(C_3H_6O)_a(C_2H_4O)_bH$$

wherein a is an integer such that the hydrophobe represented by ($C_3H_6O$) has a molecular weight of approximately 950 to 4000, and b is an integer such that the hydrophile portion represented by ($C_2H_4O$) constitutes approximately 50% to 90% by weight of the compound.

7. The method of claim 6, wherein said surface-active copolymer has the following formula:

$$HO(C_2H_4O)_b(C_3H_6O)_a(C_2H_4O)_bH$$

wherein a is an integer such that the hydrophobe represented by ($C_3H_6O$) has a molecular weight of approximately 1200 to 3500, and b is an integer such that the hydrophile portion represented by ($C_2H_4O$) constitutes approximately 50% to 90% by weight of the compound.

8. The method of claim 6, wherein said surface-active copolymer has the following formula:

$$HO(C_2H_4O)_b(C_3H_6O)_a(C_2H_4O)_bH$$

wherein the molecular weight of the hydrophobe ($C_3H_6O$) is approximately 1750 and the total molecular weight of the compound is approximately 8400.

9. The method of claim 6, wherein the perfusion medium is blood.

10. The method of claim 6, wherein the perfusion medium is a balanced salt solution.

11. The method of claim 6, wherein the organ is perfused in situ.

12. The method of claim 6, wherein the organ is perfused before transplantation.

* * * * *

UNITED STATES PATENT AND TRADEMARK OFFICE
CERTIFICATE OF CORRECTION

PATENT NO. : 5,250,294

DATED : October 5, 1993

INVENTOR(S) : Robert L. Duncan

It is certified that error appears in the above-indentified patent and that said Letters Patent is hereby corrected as shown below:

On the Title Page, item [75], please delete Alexander Duncan as inventor.

Signed and Sealed this

Twenty-fourth Day of January, 1995

Attest:

BRUCE LEHMAN

*Attesting Officer*  *Commissioner of Patents and Trademarks*